US006765105B2

(12) United States Patent
Törőcsik et al.

(10) Patent No.: US 6,765,105 B2
(45) Date of Patent: Jul. 20, 2004

(54) COMPOUND AND PHARMACEUTICAL COMPOSITION OF ANTIPLASMID EFFECT AND THE PREPARATION THEREOF

(75) Inventors: Mihály Törőcsik, Tószeg (HU); Péter Hegyes, Szeged (HU)

(73) Assignees: Gabriella Oláh, Budapest (HU); László Csapláros, Budapest (HU)

( * ) Notice: Subject to any disclaimer, the term of this patent is extended or adjusted under 35 U.S.C. 154(b) by 4 days.

(21) Appl. No.: 10/048,561
(22) PCT Filed: May 3, 2001
(86) PCT No.: PCT/HU01/00062
§ 371 (c)(1), (2), (4) Date: Aug. 5, 2002
(87) PCT Pub. No.: WO01/93843
PCT Pub. Date: Dec. 13, 2001

(65) Prior Publication Data
US 2003/0087880 A1 May 8, 2003

(30) Foreign Application Priority Data
Jun. 5, 2000 (HU) .......................................... P0002147

(51) Int. Cl.⁷ ............................... C07F 7/04; C07F 7/10
(52) U.S. Cl. ........................................ 556/413; 556/418
(58) Field of Search ................................. 556/413, 418

(56) References Cited
U.S. PATENT DOCUMENTS
5,399,727 A    3/1995  Buendia et al.

FOREIGN PATENT DOCUMENTS
GB    1 017 602 A    1/1966

OTHER PUBLICATIONS
Nabi, CA 131:227790, Acta Chromatographica, 1999, vol 9, pp. 123–132, abstract.*
* cited by examiner

*Primary Examiner*—D. Margaret Seaman
(74) *Attorney, Agent, or Firm*—Brich, Stewart, Kolasch & Birch, LLP

(57) ABSTRACT

The subject of the invention is a compound of antiplasmid effect having the general formula I

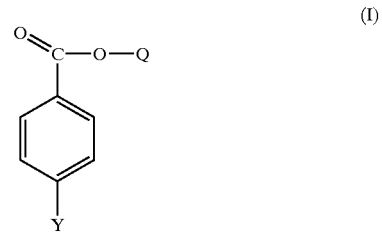

wherein
Q means: β-picolinyl-methoiodide or
1-methyl-4-piperidyl or
3-(4'-fluorophenyl)-2,2-dimethyl-2-sila-propyloxy or
2-dimethyl-amino-ethyl-methoiodide group and
Y means: 2,2-dimethyl-2-sila-hexyloxy or
3-(4'-fluorophenyl)-2,2-dimethyl-2-sila-propyloxy or
5-(4'-fluorophenyl)-4,4-dimethyl-4-sila-pentyloxy or
3-trimethylsilil-propyloxy group.

Figure 1:
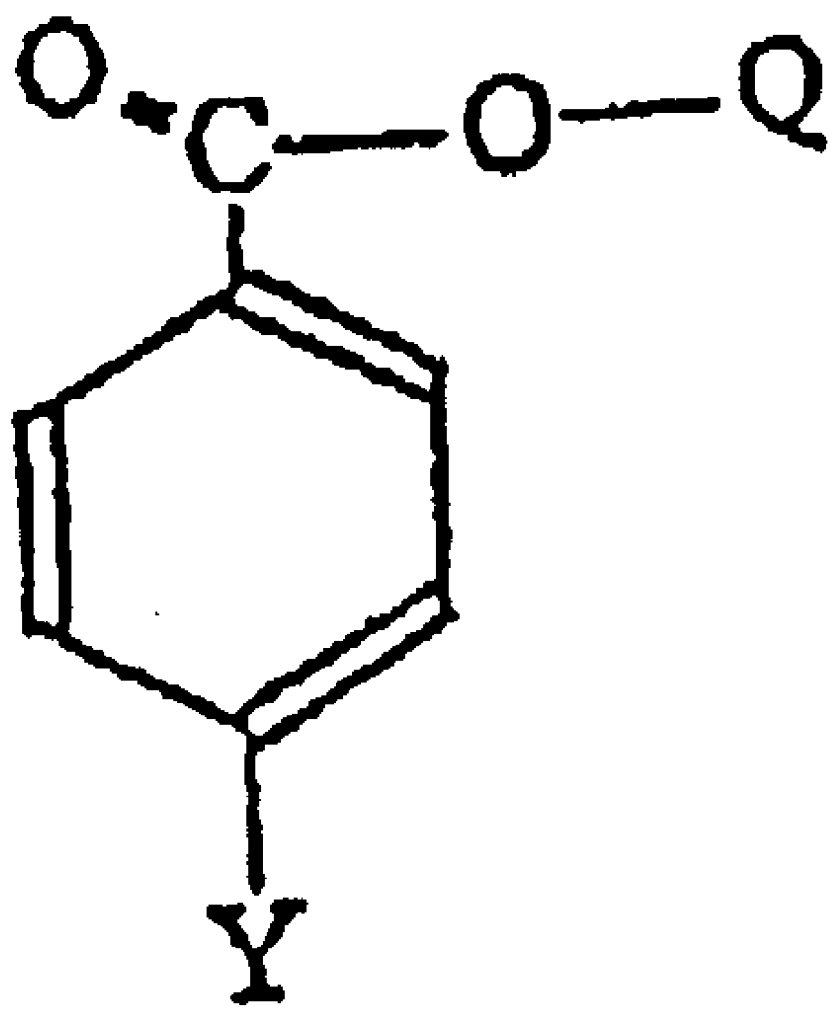

The subject of the invention is the method for producing of the above compound. The subject of the invention is also the pharmaceutical composition of antiplasmid effect, which contains the above composition and the method of producing thereof.

4 Claims, 6 Drawing Sheets

(I)

COMPOUND AND PHARMACEUTICAL COMPOSITION OF ANTIPLASMID EFFECT AND THE PREPARATION THEREOF

This application is the national phase under 35 U.S.C. § 371 of PCT International Application No. PCT/HU01/00062 which has an International filing date of May 3, 2001, which designated the United States of America and was published in English.

Several scientific publications were published about compounds of antiplasmid effect. There was no mention about antiplasmid effect of hydroxy-benzoic acids up to now in the literature, only some publications dealing with their antibacterial effect appeared in this field (e.g. *Himejima, Masaki; Kubo, Isako, J. Agric.* 1991, 39/2, 411–421.)

The importance of compounds of antiplasmid effect consists of their capability to destroy the acquired resistance of bacteria against antibiotics which can often save lives. The effect of bacteria living in the environment to the health seems unimportant for a human being while he or she is healthy. It becomes important only, when he or she gets ill because of a bacterial infection. The major part of these bacterial illnesses can be cured by means of antibiotics, but there is a growing number of infections, that are fatal because of the antibiotic resistance of the disease germ.

The phenomenon of insensibility to the antibiotics, the resistance spreads not only to human pathogenic germs, but also to pathogenic germs of animals and plants as well.

The resistance occurs among both the aerobic and anaerobic bacteria. These strains of bacteria are resistant to a multitude of antibiotics, even to those, which are reserved for the treatment of heavy infections, e.g. aminoglycosides, types of penicillin, cephalosporine and tetracycline, We set the target to produce one or more compounds with antiplasmid effect. We have found that certain hydroxy-benzoic acid derivatives have antiplasmid effect. There are some specific sorts of bacteria causing often epidemic infections, which are capable to inactivate several antibiotics.

The bacteria can be classified into three groups according to the origin of their resistance to antibiotics a) resistance pertaining to the species, which is a well-known phenomenon of some species of bacteria to some kinds of antibiotics, b) resistance, which originates from a mutation, a phenomenon of small probability with regard to a kind of antibiotic, it has a small practical importance by this reason, c) The most dangerous kind of resistance, the so-called plasmid-coupled infectious resistance is in the focus of interest, which has epidemic growth among the bacteria.

The plasmids are DNA molecules, which have special proliferation mechanism and carry genetic information independently from the chromosomes of bacteria and they are capable to transmit various properties, e.g. resistance to antibiotics, virulence and other ones.

The plasmid of resistance enables the proliferation of bacteria in the presence of an antibiotic and the bacteria can transmit this feature not only to their descendants but even to other bacteria in their environment. Such epidemic spreading of resistance to antibiotics in the bacterial flora of humans and animals is well-known since about 30 years.

The antagonistic effect to replication of plasmids of acridine paints, the ethidium bromide and the sodium dodecil sulphate was discovered by former research works, these compounds are not eligible for medical purposes because of their high toxicity. The recognition, that two well-known medicaments, chloro-promazine and prometazine eliminated the resistance to tetracycline, chloro-amphenicol and sulfonamide at 10 to 30% of bacteria culture *Escherichia coli* in vitro, underlay to the experiments aiming elimination of plasmids. The experiments were done with several well-known, in the literature described strains of bacteria cultures and cell cultures with loss of specific plasmids on specific selective culture media.

The elimination of R-plasmids and F'lac plasmids, as well as inhibition of transmission of R-plasmid transfer were studied.

The more and more extending resistance causes the research work in the field of medicaments to search continuously for new antibiotics and to supply the medicine with them.

The usage of compounds being subject of our application could result not only in a great economic benefit, but a great number of people could be successfully cured, who are actually beyond recovery because of the resistance, provided the in vivo experiments give similar results.

We found three compounds effective from 36 ones which were studied by in vitro experiments for antiplasmid effect. These are the compounds under mark FC-1181, FC-1186 and Sila-439. The compound sila-429 (75%) was compared against three representatively antibiotic resistant strains of bacteria, as follows: the polyresistant *Acinetobacter anitratus*, the resistant to gentamycine *staphylococcus aureus* and the Methycilline resistant *Staphylococcus aureus* strains.

The fact, that 3 compounds from 36 ones proved to be active in the searched effect, should be considered as an outstanding result even at international level.

We performed a preliminary study of toxicology, and established, that the mice inoculated with a dose of 50 mg/kg lived and moved vividly exactly like those in the control group, which were inoculated intraperitoneally with 0.2 ml of physiologic saline solution We used the usual dose of inoculation i.e. 0.2 ml per 10 g weight. When we augmented the dose ten times to 500 mg/kg, spasms occurred in the 5 inoculated mice in two minutes after the intraperitoneal inoculation and all the five mice died.

It can be supposed on the base of preliminary toxicological experiment that the value $LD_{50}$ is 4 to 6 times higher than the effective in vitro dose.

This latter fact should be studied in an institute dealing with toxicology and clinical pharmacology.

The experiments should be completed with examinations for plasmid elimination in an in vivo environment.

The results of experiments and calculations of quantum chemistry in relation to the examined molecules encouraged us to indicate some perspectives to design antiplasmid medicaments on the base of the relationship existing between the biological effects and the structures of molecules.

Certain compounds appeared to be promising on the base of the results of preliminary experiments and calculations. Some representatives of the mentioned groups of compounds were synthesised and examined in laboratory experiments by this reason.

The Hungarian patent specification under No. HU 180, 334 (IPC C07C 87/78) describes production of 1,1-biphenyl-2-il-alkyl-amin derivatives.

The U.S. patent specification of U.S. Pat. No. 4,695,631 (IPC C07C 87/24) describes a method for producing enamines or -imines.

Antibiotics are often used to eliminate plasmids or other elements similar to chromosomes from the host cells.

Michel, Briand and his fellow workers describe usage of several 4-quinolone derivatives (J. Antimicrob. Chemother., 18, 667–674 /1986/) included cinoxacine and novobiocine with the aim to extirpate various plasmids of resistance to medicaments from the cells of the family Enterobacteriaceae.

A special plasmid development method, a map of plasmid restriction and functions, as well as a flowchart of said method are described for producing somatotropic hormone for cattle in the US document laid open to public inspection of No. 54415/1990.

It can be established on the base of the cited sources of literature that no relevant solution was published, which affects the subject matter of the invention, they cannot be reviewed by his reason.

We tested a multitude of representatives of the group of compounds that we supposed to have antiplasmid effect, as we endeavoured to search for base of following research activity (that should be the target of the invention) to approach our aims in our targeted work but having elements of fundamental research, by means of analysis of the relationship between the chemical structure and biological effect.

We could establish a well recognisable relation to the antiplasmid effect depending on the substituents and functional groups.

We established during our experiments, that the derivatives of benzoic acid and those of benzoic acid imides having the general formula (I)

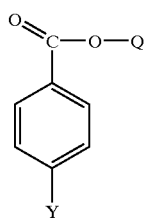
(I)

as new compounds have antiplasmid effect. The general formula (I) is shown in the FIG. 1.

The substituents of the compound are as follows:

Q means: β-picolinyl-methoiodide or 1-methyl-4-piperidyl or 3-(4'-fluorophenyl)-2,2-dimethyl-2-sila-propyloxy, or 2-dimethyl-amino-ethyl-methoiodide group and Y means: 2,2-dimethyl-2-sila-hexyloxy or 3-(4'-fluorophenyl)-2,2-dimethyl-2-sila-propyloxy or 5-(4'-fluorophenyl)-4,4-dimethyl-4-sila-pentyloxy or 3-trimethylsilil-propyloxy group.

The scope of the present invention includes the pharmaceutical compositions with antiplasmid effect and the method of their production. We performed a search for previous publications in the Chemical Abstracts under keywords "Benzamide" and "Benzoic Acid" from 1962 to June 1998 and among HU, DE, EP and US patent specifications according to classification codes specified in the application form. No anteriority was found by the novelty search where would be found the describing of the derivatives of benzoic acid and benzoic acid amides of the general formula I with the substituents as defined above. The compounds and the method of their production, as well as their application as active substance of pharmaceutical compositions are new by this reason.

The compounds described in the literature and showing only similarity to our ones deviate of the general formula (1). Such compounds are the o-dimethyl-methoxy-silil-benzoic acid methylesher and the o-trimethoxy-silil-benzoic acid trimethyl-silil-ester There-is an oxo-oxygen atom in the alkylenic chain in the compounds which contain alkylene-oxy connection. Such compound is the 2-[2-/4-morpholinyl/-2-oxo-ethoxy]-benzoic acid-amid The 3-[2-n-butyl-1-{/trimethyl-silil-/ethoxy-methyl}-1H-imidazol-5-il]-benzoic acid-methyl ester differs from the compounds of the general formula (I) by the ethoxy-methyl-imidazolyl attachment between the silicon atom and the basic frame. The 2-formyl-5-methoxy-6-methyl-3-[dimethyl-/1,1,2-trimethyl-propyl/-silanol-oxy]-benzoic acid-allyl ester differs by its polysubstituted ring from the compounds required by the present application. The defined compounds show considerable antiplasmid effect in experiments in vitro. The compounds Sila-439 (75%9 and FC-2006/C have among others outstanding plasmid eliminating ability (in concentration of 50 μg/ml). The compounds characterised by the general formula (I) are not only new, but they are unknown and not described in the literature, as there is not even any reference to them in the literature. The compound Sila-439 i.e. 4-(3-trimethyl-silil-propyloxy)-benzoic acid-2-dimethyl-amino-ethyl-ester-methoiodide has an extraordinary good eliminating ability The compounds marked by FC 2006/C and FC 2012 have good eliminating ability, as well.

The compound FC 2006/C is 4(dimethyl-n-butyl-silil-methyloxy)-benzoic acid-(3-pyridyl)-methylester-methoiodide.

The compound FC 2012 is 4-(dimethyl-n-butyl-silil-methyloxy)-benzoic acid-3-dimethylamino-propyl-ester-methoiodide.

The importance of these compounds is that they are capable to eliminate the acquired resistance of bacteria against antibiotics, and the said elimination can save lives.

On the one hand the compounds of the invention are capable to eliminate the plasma which causes the resistance; on the other hand they can hinder, that the plasma of resistance will be transmitted from the bacteria of "infectious" to the "healthy" bacteria and an "epidemic" would be created.

The compound Sila-439 is suitable to registration as medicament because its eliminating effect is more extended.

The eliminating effect of the compound FC-2006/C is almost 100% but only to one E. coli plasmid.

| Eliminating compound | MIC mg/ml | Results of elimination of FC-2006/C, FC-2012 | | | |
|---|---|---|---|---|---|
| | | Concentration of elimination mg/ml | Frequency of elimination | | (%) |
| | | | TC | ApTC | Lac |
| Ethidium bromide | 125 | 62,5 | 30 | 24 | 0 |
| | | 312, | 10 | 0 | 0 |
| FC-2006/C | 25 | 18 | 0 | 0 | 0 |
| | | | 0 | 0 | 0 |
| FC-2012 | 39 | 33 | 58 | 27 | 0 |
| | | 25 | 10 | 2 | 0 |

Methods Used:

The bacteriostatic effect was inspected on a liquid culture medium using method of serial dilution. We inoculated 0.05 ml of culture of the examined bacteria being in exponential phase (i.e. of optical density 0.4) in dilution by $10^{-4}$ into broth culture medium MTE of 5 ml. The culture of E. coli of optical density 0.4 contained 4.1 to $5.2 \times 10^8$, the one of Staphylococcus aureus of similar density contained 2.2 to $8.2 \times 10^7$ settlement building units per ml. The culture medium units infected by the same number of bacteria and containing different quantities of compounds (0 to $30 \times 10^{-4}$ M) being examined were kept at the temperature 37° C. during 18 hours. We examined thereafter the smallest concentration of each compound, which still inhibits the proliferation of the identical number of bacteria. The examinations for the antiplasmid effect could be begun after having been obtained the mentioned date, because these effects can be detected only at values lower than MIC.

The Elimination of R-Plasmid:

We made a dilution of $10^{-4}$ from a preliminary culture of 16 hours of *E. coli* strains containing R-factor, and dosed 0.05 ml therefrom into a broth culture medium MTE of 5 ml. We completed the cultures with the examined compounds in different concentrations and kept them at the temperature 37° C. during 24 to 48 hours without aeration. We made different dilutions from the cultures and streaked 0.1 ml of them onto EP agar plates. Having incubated them during the night we made a replication from the plates containing the cultures onto plates containing the corresponding antibiotics.

The plates containing antibiotics were incubated at 37° C. during 24 hours then the settlements of bacteria on them were compared to those on the master plates and the requirement of nutrition of the bacteria was examined.

The Elimination of F'lac Plasmid

We made a dilution of $10^{-4}$ from a culture of 16 hours of the bacteria strain K12 LE140 of *E. coli* and we inoculated 0.05 ml (1 to $5 \times 10^3$ cells) of it into 5 ml of broth culture medium MTE. The cultures with plasmid eliminating compounds added in different concentrations were incubated at 37° C. during 24 hours. We made dilutions from the contents of tubes, in which growth of bacteria were detected, then 0.1 ml of these dilutions were streaked onto EMB agar. The plates were incubated at 37° C. during 24 hours, then we counted the settlements of bacteria of types lac$^+$ and lac$^-$, which provides basis to calculate the percent of inhibition.

The Inhibition of R-Plasmid Transfer

We made tenfold dilutions of fresh donor culture of E. coli C600 R144 drd-3 and of fresh recipient culture resistant to i$^r$ and in some cases to nalid-x acid of *E. coli* K12 W1 at optical density of 0.4 (60 nm), then we mixed together 1.0 ml of donor culture and 1.0 ml of recipient culture and kept the samples at the temperature 37° C. 0 to 24 hours in presence of the applied compounds.

As control the mixture of donor and recipient cultures of the same proportion was incubated.

We performed experiments of two types to clarify the manner of action. The donor cells were previously treated during 5 minutes with the compound to be examined being in corresponding concentration, and the recipient cells were added thereafter in the experiments of one type The compounds to be examined were added 5 minutes after mixing together the donor and recipient cultures in the experiments of the other type. The target of our examinations was the inhibition of the conjugated transfer at the formed pairs. We made tenfold dilutions of the samples with physiological saline solution, the formed pairs of cells were divided by shaking during 1 minute then we made following dilutions where no more resistance transfer passed (see. Beverley and fellow-workers, 1981).

We streaked quantities of 0.1 ml form the dilutions onto MTE agar plates containing 50 µg/ml of kanamycine and onto plates containing 500 µg/ml of sodium azide to determine the number of recombinants. The number of donor bacteria was established only on the culture medium containing kanamycine, the number of recipient ones was established only on the culture medium containing sodium azide. The plates were kept during 48 hours at 37° C.

The more and more extending resistance causes the research work in the field of medicaments to make enormous investments to search continuously for new antibiotics and to supply the medicine with them.

We performed preliminary examinations of toxicity of the compound Sila-439 having very good plasmid elimination effect (the 7.0 g of material which was handed), because it has not only the above mentioned effect, but a considerable antibacterial one, too.

The previously established MIC (minimal inhibiting concentration) values are as follows:

for *Escherichia coli* (resistant to Chlorocid) 70 µg/ml, for *Acinetobactes anitratus* (resistant to Chlorocid) 80 µg/ml, for *Staphylococcus aureus* (resistant to gentamycine) 180µ/ml.

The antiplasmid effect manifests at the concentration 40 µg/ml.

We performed preliminary studies of toxicity and established, that the mice inoculated with a dose of 50 mg/kg lived and moved vividly exactly like those in the control group, which were inoculated intraperitoneally with 0,2 ml of physiologic saline solution.

We used the usual dose of inoculation i.e. 0,2 ml per 10 g weight. When we augmented the dose ten times to 500 mg/kg, spasms occurred in the 5 inoculated mice in two minutes after the intraperitoneal inoculation and all the five mice died. It can be supposed on the base of preliminary in vivo toxicological experiment that the value $LD_{50}$ is 4 to 6 times higher than the effective in vitro dose. The exact definition of this value should be done in an institute dealing with toxicology and clinical pharmacology.

| Dose | | Toxicity (i.p) of Sila-439 | | | | |
|---|---|---|---|---|---|---|
| | | Incubation (hours) | | | | |
| ml/mouse | mg/kg | 2 | 6 | 9 | 12 | 24 |
| 0.00 control | 0.00 | 5/5 | 5/5 | 5/5 | 5/5 | 5/5 |
| 0.01 | 50 | 5/5 | 5/5 | 5/5 | 5/5 | 5/5 |
| 0.1 | 500 | 0/5 | — | — | — | — |

The mice used in the experiment weighted 46 to 50 g according to CELP.

The usage of compounds being subject matter of our application could result not only in a great economic benefit, but a great number of people could be successfully cured, who are actually beyond recovery because of the resistance.

The subject matters of the invention are as follows.

A compound of antiplasmid effect having the general formula (I)

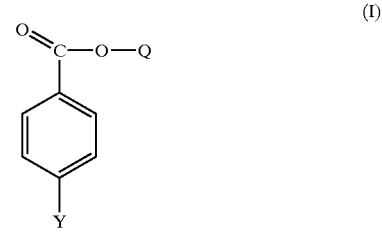

(I)

characterised by that in the general formula

Q means: β-picolinyl-methoiodide or 1-methyl-4-piperidyl or 3-(4'-fluorophenyl)-2,2-dimethyl-2-sila-propyloxy, or 2-dimethyl-amino-ethyl-methoiodide group and Y means: 2,2-dimethyl-2-sila-hexyloxy or a 3-(4'-fluorophenyl)-2,2-dimethyl-2-sila-propyloxy or 5-(4'-fluorophenyl)-4,4-dimethyl-4-sila-pentyloxy or 3-trimethylsilil-propyloxy group.

The subject of the invention is the method for producing a hydroxy-benzoic acid derivative of the general formula (I) wherein Q and Y have the same meaning as defined above. The method is characterised by that a) 4-hydroxy-benzoic acid ester is brought into reaction with such an organic halogen compound which provides a group Y as defined in the claim 1 under appropriate reaction circumstances, b) the obtained 4-alkoxy-benzoic acid ester is hydrolysed into carboxylic acid, c) the obtained 4-alkoxy-benzoic acid is transformed with a well-known method to acid chloride, d) the obtained acid chloride is brought into reaction with such an amino-alcohol which provides a group Q as defined in the claim 1, e) and the obtained amino-alcohol-ester is transformed into quaternary compound with methyl iodide—if necessary.

The subject matter of the invention is a pharmaceutical composition of antiplasmid effect characterised by that it contains the hydroxy-benzoic acid of the general formula where the meanings of Q and Y are the same as defined above, as an active substance.

The subject matter of the invention is also a method for producing a pharmaceutical composition characterised by that an effective quantity of the hydroxy-benzoic acid derivative of the general formula I wherein the meanings of Q and Y are the same as defined above is mixed with usual pharmaceutical ingredients.

The practical embodiment of the method according to invention is illustrated by the following examples

EXAMPLE 1

Sila-439/A (+Si$^{++++}$)

4-(dimethyl-n-butylsilil-methoxy)-benzoic acid-(3-pyridyl)-methyl-ester-methoiodide 2.8 g (10 mmoles) of 4-dimethyl-n-butylsilil-methyloxy)-benzoic acid-methyl-ester (boiling point: 170 to 172° C.) is dissolved in 50 ml of absolute benzene then 2.0 g (18 mmoles) of 3-hydroxy-methyl-pyridine and some drops of sodium methylate solution are added then the mixture is heated on reflux during two hours. A still head is attached onto the alembic and the solvent is distilled at atmospheric pressure. The remaining viscous material is divided in a separating funnel between water and ether. The phase of ether is washed with 4×15 ml of water, dried on heated $Na_2CO_3$ and the ether is distilled. The remaining oily part is dissolved in acetone, 1,7 ml methyl-iodide is added, it is allowed to stand during 5 hours at room temperature then it is heated on reflux during 4 hours. It is diluted with 10 ml absolute ether after cooling. It crystallises during standstill. It is crystallised from acetone/ether. 2.5 g of slightly yellowish crystals are received of MP 88 to 89° C.

The empirical formula is $C_{21}H_{30}INO_3Si$ (499.479) the calculated percentages are as follows: C 50.50%, H 6.05%, I 25.40%. The found percentages are: C 49.86%, H 6.34%, I 24.6%.

Results of elemination with RN 4220 *S. aureus* strains containing staphylococcus plasmides

| Plasmid | Eliminating substance | Concentration (µg/ml) | Frequency of elimination (%) |
| --- | --- | --- | --- |
| pCRG 1600 | — | | 2.1 |
| | Ethidium bromide | 62.5 | 2.8 |
| | FC-2006/C | 9.5 | 32.6 |
| | FC-2012 | 7.8 | 10.1 |
| pIP 855 | — | | 1.8 |
| | Ethidium bromide | 1.95 | 9.4 |
| | FC-2006/C | 9.5 | 69.2 |
| | FC-2012 | 7.8 | 41.9 |
| pIP 856 | — | | 2.3 |
| | Ethidium bromide | 1.95 | 12.3 |
| | FC-2006/C | 9.5 | 75.1 |
| | FC-2012 | 7.8 | 34.6 |
| pBI 109 PGL | — | | 68.7 |
| | Ethidium bromide | 3.9 | 88.2 |
| | FC-2006/C | 9.5 | 94.4 |
| | FC-2012 | 7.,8 | 88.0 |

The transfer inhibiting effect of the compounds FC-2006/C and FC-2012

| | | Frequency of transfer | | | |
| --- | --- | --- | --- | --- | --- |
| Donor | Recipient | Without substance | FC-2006/C* | Without substance | FC-2012 |
| *E. coli* K 12 F'lac1 Sm$^r$, nal$^3$, lac$^+$ | *E. coli*χ1037 F-lac$^-$ nal$^r$ | $0.6 \times 10^{-6}$ | $2.2 \times 10^{-6}$ | $0.8 \times 10^{-6}$ | 0** |
| *E. coli* K12 F'lac2 | *E. coli*χ1037 F-lac$^-$ nal$^r$ | $0.6 \times 10^{-6}$ | $3 \times 10^{-6}$ | $0.2 \times 10^{-5}$ | 0** |
| *E. coli* K12 J5-3 (R386) Inc: FI Tc$^r$, nal$^a$ | *E. coli*χ1037 F-lac$^-$ nal$^r$ | $0.5 \times 10^{-1}$ | $0.9 \times 10^{-2}$ | 0.4 | $0.6 \times 10^{-1}$*** |
| *E. coli* K12 J5-3 (R16) Inc: 0 Tc$^r$, Ap$^r$ | *E. coli*χ1037 F-lac$^-$ nal$^r$ | $0.3 \times 10^{-1}$ | $0.3 \times 10^{-3}$ | $1.2 \times 10^{-2}$ | $1 \times 10^{-3}$*** |
| *E. coli* K12 J5-3 (R27) Inc: H Tc$^r$ | *E. coli*χ1037 F-lac$^-$ nal$^r$ | $0.2 \times 10$ | $0.2 \times 10^{-1}$ | $2.5 \times 10^{-4}$ | $2.3 \times 10^{-4}$*** |

Figure 2:
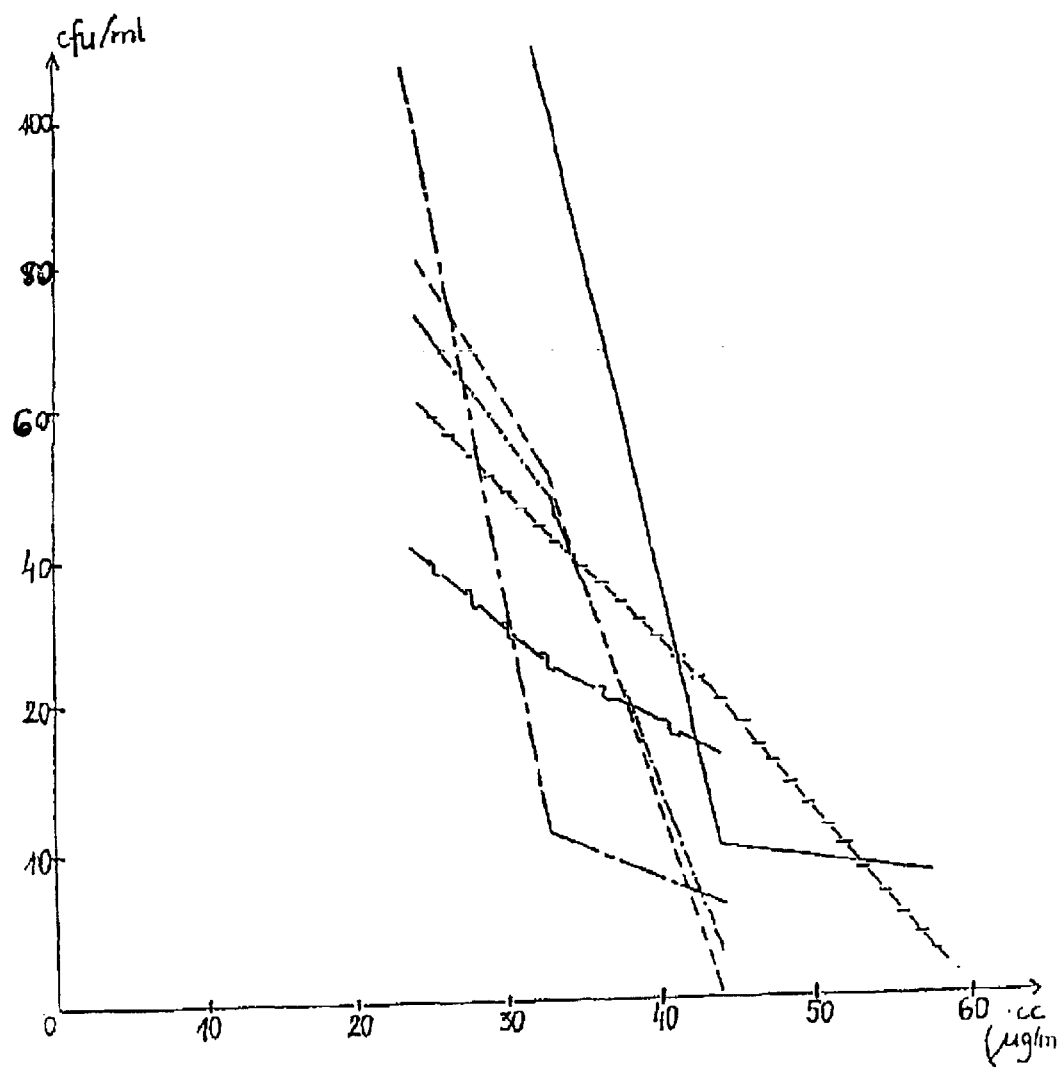

*in concentration of 24.7 µg/ml,
**in concentration of 15 µg/ml;
***in concentration of 30 µg/ml The effects of compounds are shown in the attached figures In the FIG. 2 the values of effect of FC-2006/C and FC-2012 are shown against E. coli K15 JS-3 strains containing R386, R16 and R27 plasmids The meanings of lines: treated with FC-2006/C:

R386 _____

R16: - - - - - - - - -

R27: -.-.-.-.-.-

Treated with FC-2012:

R386: - - - - - - - - - -

R16: -/-/-/-/-/-

R27: -\-\-\-\-\-

Figure 3:
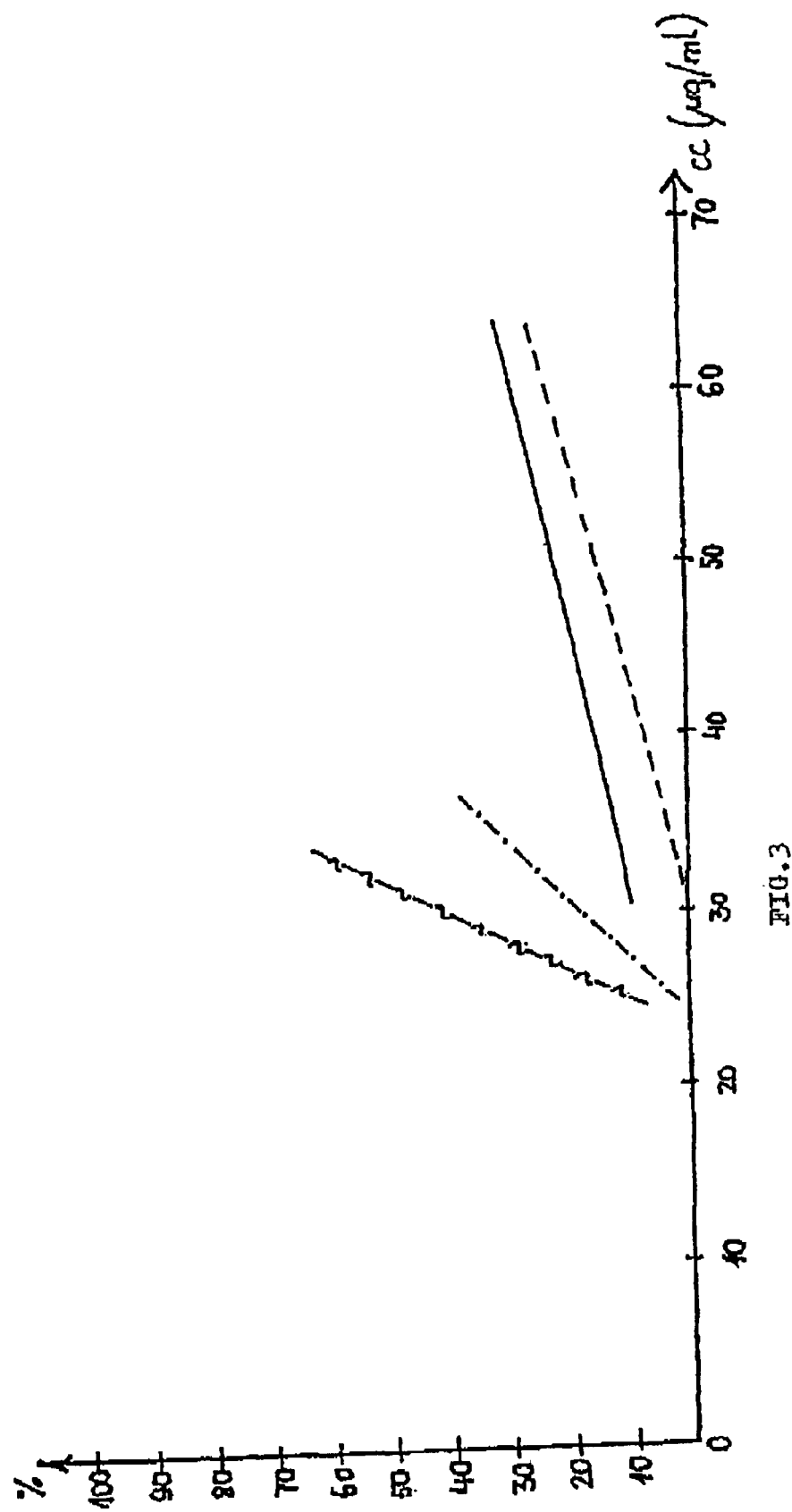

In the FIG. 3 the frequency of elimination of E. coli K12 F'lac (PBR322) plasmid with FC-2012 and ethidium bromide is shown The meanings of lines:
EB (eliminating Tc): _____
EB (eliminating ApTc): - - - - - -
FC-2012 (eliminating Tc): -\-\-\-
FC-2012 (eliminating ApTc): -.-.-.-

Figure 4:
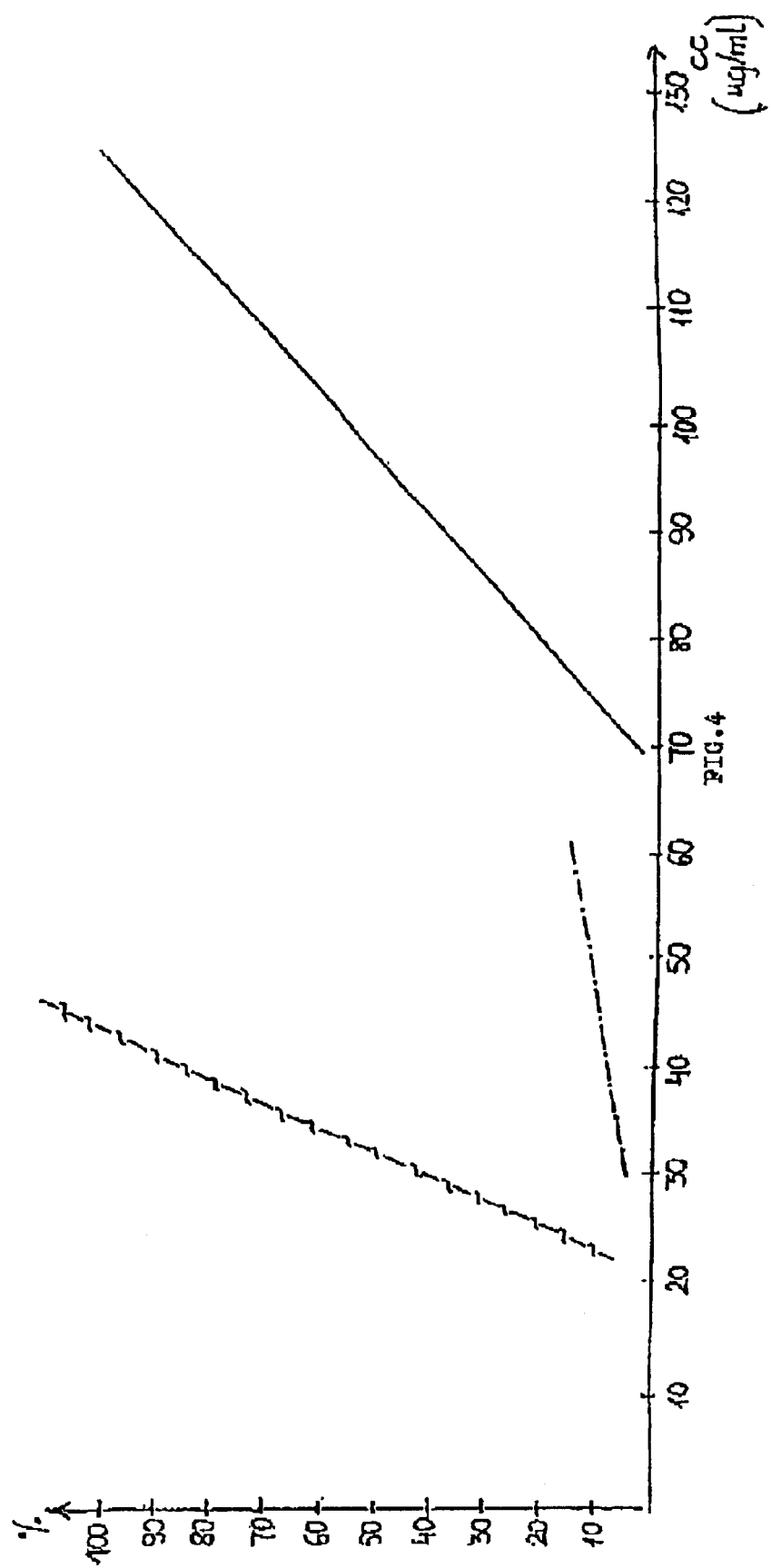

In the FIG. 4 the frequency of elimination of E. coli K12/317 (PBR322) with FC-2012 and ethidium bromide is shown The meanings of lines:
EB (eliminating Tc): _____
FC-2012 (eliminating Tc): -\-\-\-
FC-2012 (eliminating ApTc): -.-.-.-

Figure 5:
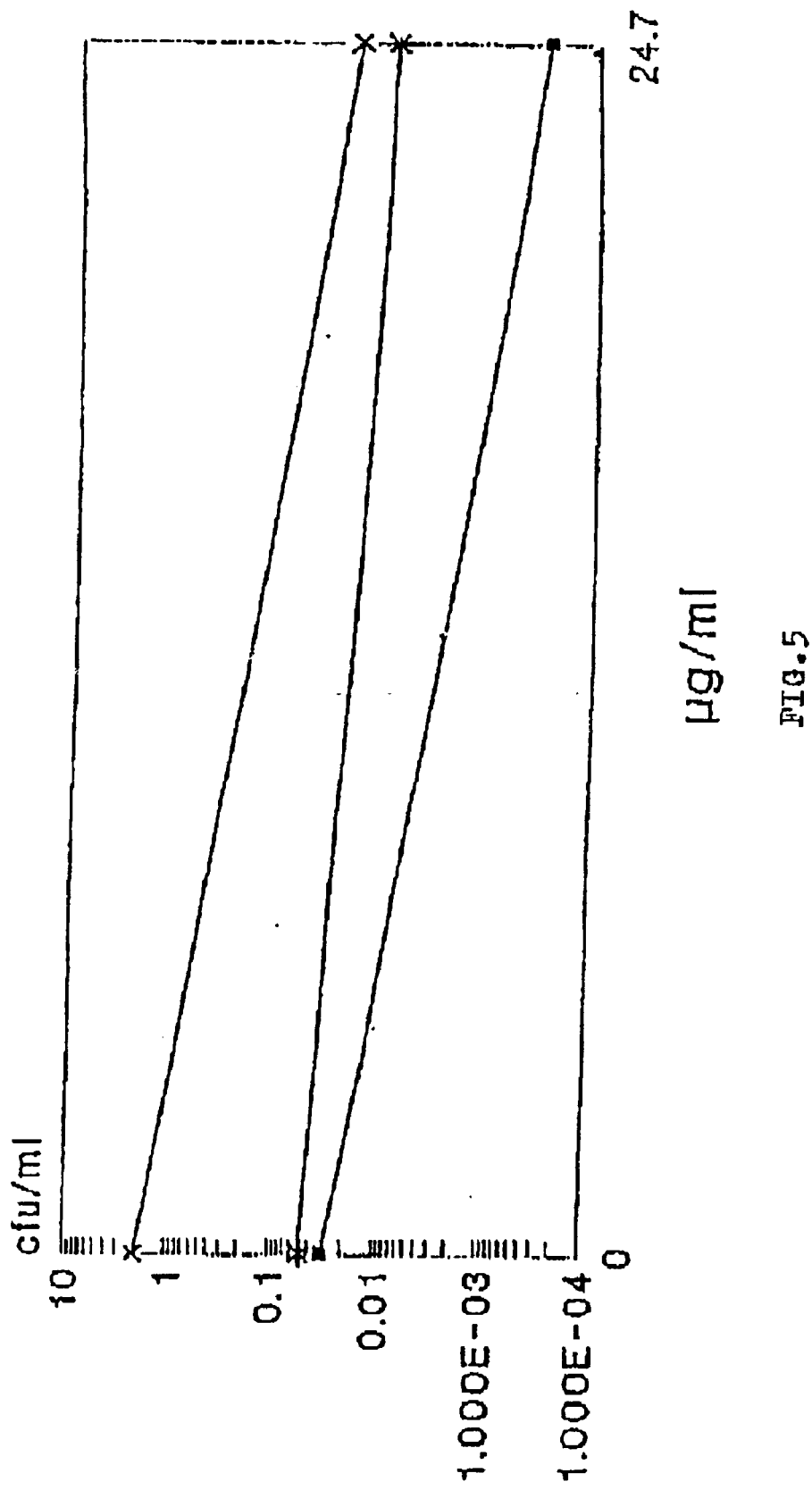

In the FIG. 5 the frequency of transfer is shown under influence of the substance marked with FC-2006/c Transferred plasmid: the meanings of marks: -*-R386, -□-R16, -x-R27.

Figure 6:
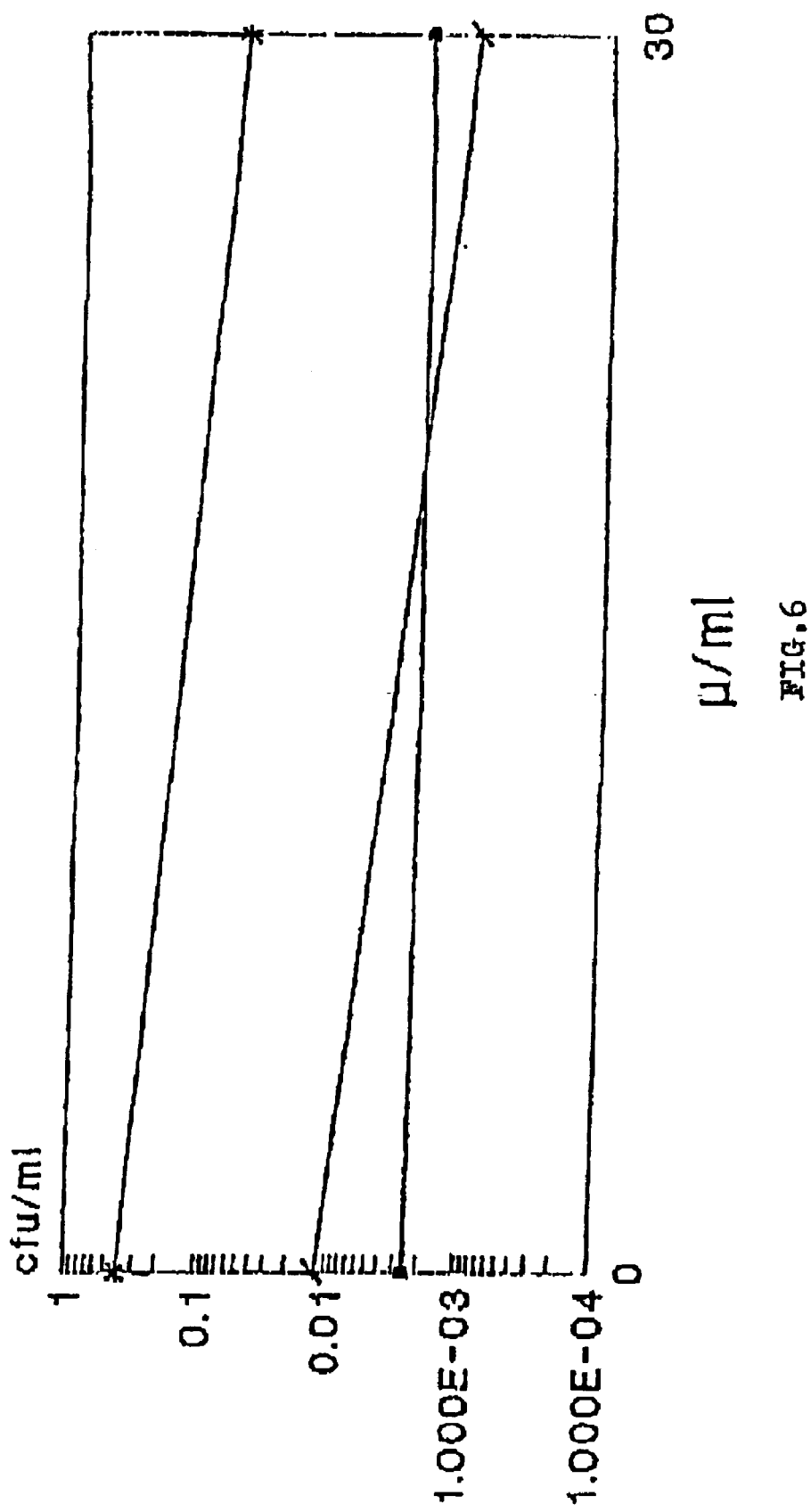

In the FIG. 6 the frequency of transfer is shown under influence of the substance marked with FC-2012. Transferred plasmid: the meanings of marks: -*-R386, -□-R27, -x-R16.

What is claimed is:

1. A compound of antiplasmid effect having the general formula (I)

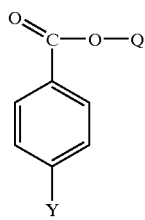

(I)

wherein in the general formula,

Q is 2-dimethyl-amino-ethyl-methoiodide, and

Y is selected from the group consisting of 2,2-dimethyl-2-sila-hexyloxy, 3-(4'-fluorophenyl)-2,2-dimethyl-2-sila-propyloxy, 5-(4'-fluorophenyl)-4,4-dimethyl-4-sila-pentyloxy, and 3-trimethylsilil-propyloxy.

2. A method for producing a hydroxy-benzoic acid derivative of the general formula (I)

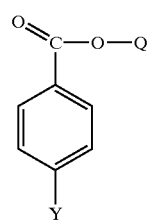

(I)

wherein Q and Y have the same meaning as defined in claim 1 comprising the steps of:

(a) reacting 4-hydroxy-benzoic acid ester with such an organic halogen compound which provides a group Y as defined in claim 1 under appropriate reaction conditions, (b) hydrolyzing the obtained 4-alkoxy-benzoic acid ester into carboxylic acid, (c) transforming the obtained 4-alkoxy-benzoic acid into acid-chloride, (d) reacting the obtained acid chloride with such an amino-alcohol which provides a group Q as defined in claim 1, and optionally (e) transforming the obtained amino-alcohol-ester quaternary compound with methyl iodide.

3. A pharmaceutical composition of antiplasmid effect comprising a hydroxy-benzoic acid of the general formula I

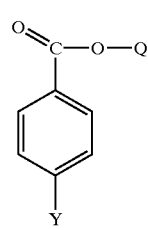

(I)

as an active agent, where the meanings of Q and Y are the same as defined in claim 1.

4. A method for producing a pharmaceutical composition comprising the step of mixing an effective quantity of a hydroxy-benzoic acid derivative of the general formula I

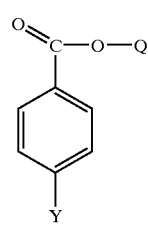

(I)

wherein the meanings of Q and Y are the same defined in claim 1, with usual pharmaceutical ingredients.

* * * * *